United States Patent [19]

Uchida et al.

[11] Patent Number: 4,780,419

[45] Date of Patent: Oct. 25, 1988

[54] METHOD OF INHIBITING GLYCOLYSIS IN BLOOD SAMPLES

[75] Inventors: Kazuo Uchida, Kobe; Shyoji Okuda, Nagaokakyo; Kiko Tanaka, Ibaraki, all of Japan

[73] Assignee: Terumo Corporation, Tokyo, Japan

[21] Appl. No.: 860,988

[22] Filed: May 8, 1986

[30] Foreign Application Priority Data

May 10, 1985 [JP] Japan .................. 60-100161

[51] Int. Cl.⁴ .................. G01N 33/48; G01N 33/66
[52] U.S. Cl. .................. 436/176; 436/8; 436/18; 436/811; 436/826; 422/41; 435/2
[58] Field of Search .................. 436/176, 8, 18, 811, 436/810, 826, 67, 87; 422/41; 435/2

[56] References Cited

U.S. PATENT DOCUMENTS

| | | | |
|---|---|---|---|
| 3,228,838 | 1/1966 | Rinfret et al. | 435/2 X |
| 3,607,077 | 9/1971 | Hartel et al. | |
| 3,979,262 | 9/1976 | Hunziker. | |
| 4,098,574 | 7/1978 | Dappen. | |
| 4,455,299 | 6/1984 | Grode | 435/2 X |
| 4,551,427 | 11/1985 | Draeger et al. | |
| 4,585,735 | 4/1986 | Meryman et al. | 435/2 |

FOREIGN PATENT DOCUMENTS

| | | |
|---|---|---|
| 0120220 | 10/1984 | European Pat. Off. |
| 0202543 | 11/1986 | European Pat. Off. |
| 1813848 | 7/1970 | Fed. Rep. of Germany |
| 2007637 | 1/1970 | France |
| 2261528 | 9/1975 | France |
| 0618386 | 8/1973 | Japan |
| 6053845 | 1/1982 | Japan |
| 1227925 | 4/1971 | United Kingdom |

OTHER PUBLICATIONS

Williamson, John R., "Glycolytic Control Mechanisms", J. of Biol. Chem., vol. 242, No. 19, pp. 4476–4485, 1967.

Sigler, K. et al, "Effect of Inhibitors on Acid Production by Baker's Yeast", Folia Microbiol., vol. 23, No. 6, pp. 409–422, 1978.

Dietzler et al, "Carbohydrates", Gradwohl's Clinical Lab. Methods and Diagnosis, vol. 1, p. 222, 1980.

*Primary Examiner*—Michael S. Marcus
*Assistant Examiner*—Lynn M. Kummert
*Attorney, Agent, or Firm*—Burns, Doane, Swecker & Mathis

[57] ABSTRACT

There is described a method of inhibiting glycolysis in blood samples by adding an acid to the blood sample to adjust pH of the blood to a level between 5.0 and 7.0.

Collected blood samples undergo glycolysis during storage due to progress of the reaction with glycolytic enzymes with a result that glucose is reduced and lactic acid and pyruvic acid formed by the glycolysis is increased. According to the method of the invention, the glycolysis as mentioned above can be inhibited simply by adjusting pH of the blood sample so that accurate determination of the above-mentioned components are feasible. The preferred acids are citric acid, malonic acid and maleic acid. Addition of citric acid to produce a level between 1.0 and 5.0 mg/ml (blood) is especially preferable. In the method of the invention, further addition of a fluoride compound, preferably NaF, improves the glycolysis-inhibiting action.

The method of the invention is preferably carried out by the use of blood-collection tubes in which an acid in an amount sufficient to adjust pH of the blood sample to a level between 5.0 and 7.0, and additionally, a fluoride compound are contained therein.

6 Claims, 2 Drawing Sheets

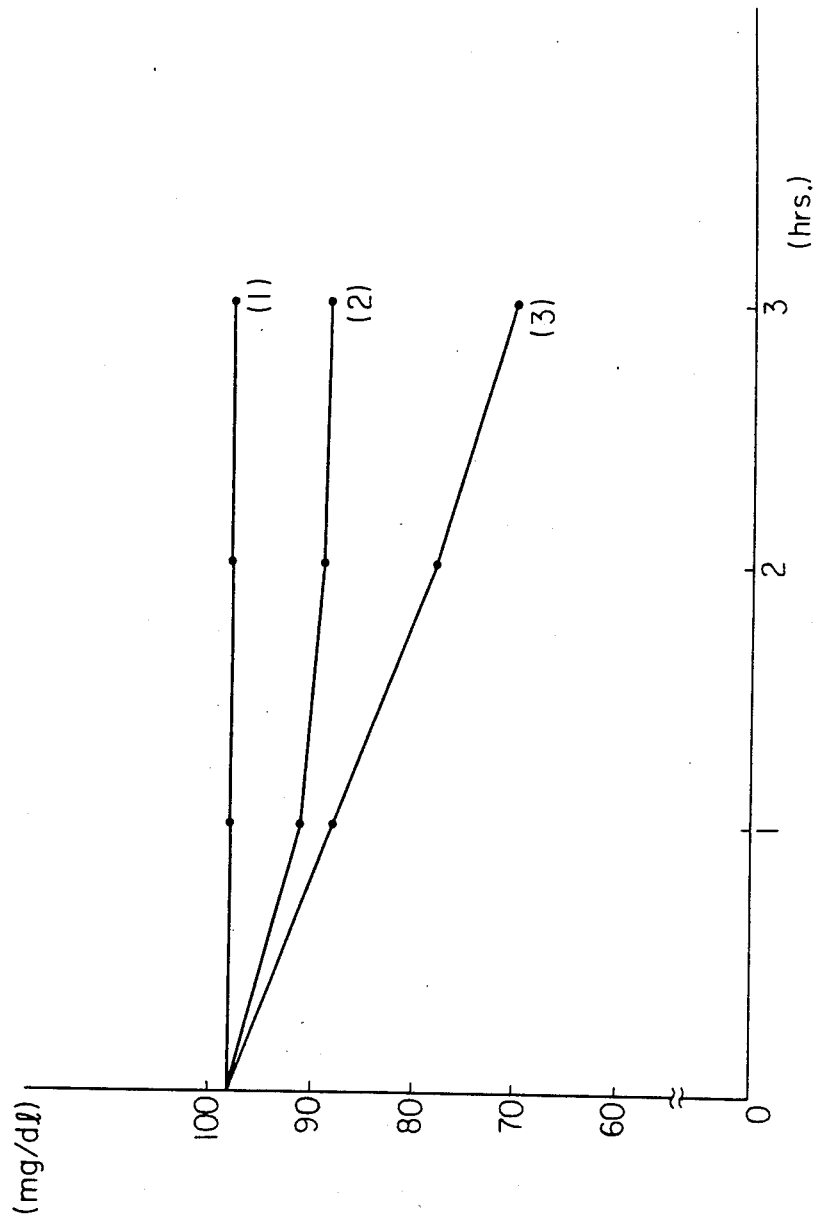

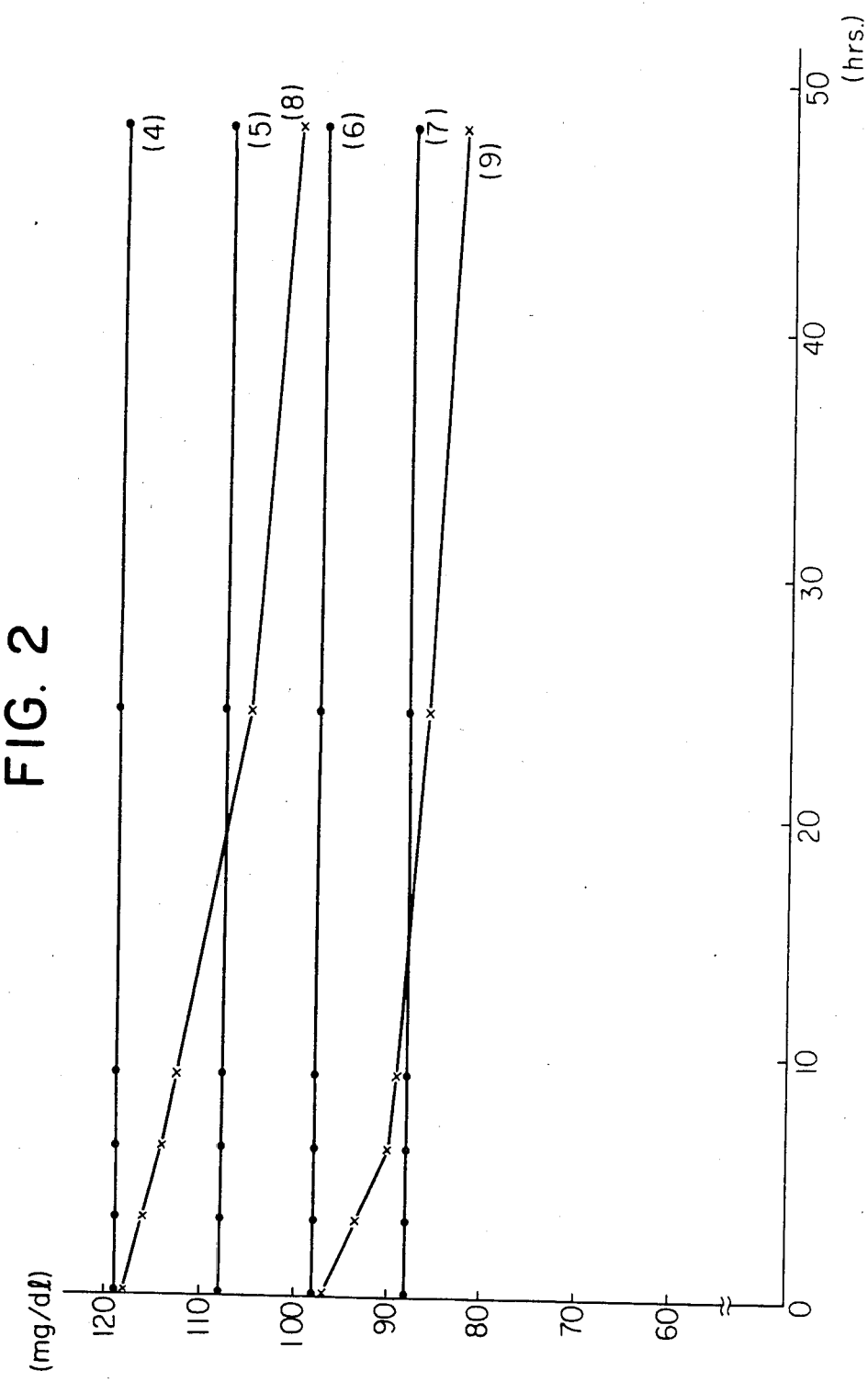

METHOD OF INHIBITING GLYCOLYSIS IN BLOOD SAMPLES

BACKGROUND OF THE INVENTION

1. Field of the Invention

The present invention relates to a method of inhibiting glycolysis of glucose in blood samples.

In the determination of glucose, lactic acid or pyruvic acid in blood samples, if collected blood samples are allowed to stand at room temperature, glycolysis reactions with glycolytic enzymes in blood will proceed with a result that glucose is decreased and lactic acid and pyruvic acid formed by the glycolysis are increased. These reactions are known as so-called Embden-Meyerhof pathway. It has also been experimentally indicated by us that glucose in blood stored at 37° C. is decreased from an initial value of 110 mg/ml to ca. 83 mg/ml after 3 hours. Usually, as time needed between the blood collection and the analytical operation is at least 2 to 3 hours (in case of analysis at hospitals) or occasionally dozens of hours (in case of analysis at other laboratories), it is required to inhibit the glycolysis reactions as described above. The method according to the invention provides means effectively used for the analysis of such blood components.

2. Description of Prior Arts

Heretofore, inhibition of glycolysis reactions in blood samples is known to be effected by (1) a method by which a glycolysis inhibitor principally consisting of a fluoride compound is added, (2) a method by which plasma and enzyme-containing blood cells are separated immediately after blood collection, (3) a method by which deproteination is carried out rapidly after blood collection or (4) a method by which blood samples after collection are stored at a low temperature. All of the methods (2), (3) and (4), however, are troublesome in handling of samples immediately after blood collection or transport and storage of blood samples. The method (1) is widely employed, because the fluoride compound used therein such as, for example, sodium fluoride (NaF) or potassium fluoride (KF) is believed to be a specific inhibitor of enolase (an enzyme) which acts in the course of Embden-Meyerhof glycolysis pathway and is used in the form of a very small amount of powders placed in advance in a sample-collecting vessel for easy mixing with blood sample. A blood-collecting tube widely employed in practice for this purpose is VENOJECT (FH) (tradename of a product manufactured by Terumo K.K.) in which powders principally consisting of NaF are placed. In this method, as F ions from NaF at a higher concentration induce elution of hemoglobins from blood cells, that is, hemolysis, NaF is added in an amount to produce concentration as low as 1.25 mg/ml or below.

Though many studies have been made on the optimal conditions for the use of fluorine compounds as a glycolysis inhibitor, there remains questions as to whether fluoride compounds are satisfactory with respect to time required for onset of the glycolysis-inhibiting action as well as to duration of the glycolysis-inhibiting action. As shown by line (2) in FIG. 1 of the attached drawing, it has experimentally been demonstrated by us that the glucose level in blood to which 1.25 mg/ml (blood) of NaF (corresponding to the amount incorporated in VENOJECT (FH) manufactured by Terumo K.K. cited above) has been added is reduced by ca. 6% in 1 hour and by ca. 8% in 3 hours. The reduction to such degrees is pointed out also by Tatsuo Nagashima and others in an article entitled "Glycolysis inhibition in blood glucose determination" appearing in Japanese Journal of Medical Technology (special volume for the 33rd Congress of Japanese Association of Medical Technologist, Vol. 33, No. 3, published Mar. 25, 1984) p. 463. As described above, glycolysis inhibition by means of the prior-art glycolysis inhibitors is questionable regarding rapid onset and duration of the action. It has been confirmed by ion chromatographic analysis that F and I ions such as those from the fluoride compounds widely used as the glycolysis inhibitor and monoiodoacetic acid are easily and rapidly passed through the cell membrane of red blood cell to be introduced in the cell in which glycolytic enzymes are present. Therefore, longer time required for onset of the action of the prior-art glycolysis inhibition is believed not due to their cell-membrane permeability but to the fact that the enzyme (enolase) on which these inhibitors act is not a rate-determining enzyme for the glycolysis system.

SUMMARY OF THE INVENTION

It is an object of the present invention to provide a method of inhibiting glycolysis of glucose in blood samples during storage.

A further object of the invention is to provide blood-collection tubes suitable for use in the above-mentioned method.

These objects of the invention are achieved by adjusting pH of blood to a level between 5.0 and 7.0 by the addition of an acid to the blood samples. As the acid are preferable organic acid, especially citric acid. The objects of the invention are better achieved by further adding a fluoride compound to the blood samples. Furthermore, they are achieved by the use of blood collection tubes in which the acid in an amount sufficient to adjust pH of the sample to a level between 5.0 and 7.0 is contained.

BRIEF DESCRIPTION OF THE DRAWING

FIGS. 1 and 2 are graphic presentations of the relationship between glucose concentration in blood samples and storage time of the samples.

FIG. 1 indicates a case at the storage of the samples at 37° C., and FIG. 2 indicates a case at the storage of the samples at room temperature.

In FIG. 1, the lines (1), (2) and (3) indicate changes of the glucose concentration when the same blood sample was collected and stored respectively in a blood collection tube of the invention (Example 4), VENOJECT (FH) and a blood collection tube in which EDTA·2Na alone is contained. In FIG. 2, the lines (4)–(7) indicate changes of glucose concentration when different blood samples are collected respectively in each of blood collection tubes of the invention, and the lines (8) and (9) indicate those respectively in each of VENOJECT (FH).

DETAILED DESCRIPTION OF THE INVENTION

As a result of extensive studies to overcome the above-mentioned disadvantages of the prior-art methods of inhibiting glycolysis in blood samples, we have found that rapid onset of the glycolysis-inhibiting action can be realized by the effect of pH reduction (acidification) to inhibit phosphofructokinase of the group of enzymes participating in the glycolysis pathway. We have further found that combined use of a fluoride compound added in a minimum amount with the above-mentioned acid enables a great improvement in duration of the glycolysis-inhibiting action. The present invention has been completed on the basis of these findings.

The invention is directed to a method of inhibiting glycolysis in blood samples by adjusting pH of blood to a level between 5.0 and 7.0 by the addition of an acid to blood samples collected for the determination of glucose, lactic acid or pyruvic acid contained therein. Furthermore, it is directed to a method of inhibiting glycolysis in blood samples by which the glycolysis inhibiting action is strengthened by combined use of a fluoride compound added in a very small amount with the acid.

As described by Naotaka Hamazaki and Shigeki Minakami in an article entitled "Functions and metabolism of red blood cells" (Japanese Journal of Clinical Chemistry, vol. 5, No. 8, pp. 251-259, 1977), it is known that phosphofructokinase is an enzyme participating in an initial reaction stage of Embden-Meyerhof pathway (glycolysis pathway) which is much influenced by pH. The article, however, gives no suggestion at all regarding rapid onset of the glycolysis-inhibiting action as well as regarding use of the inhibiting action for the storage of blood samples in the determination of glucose, lactic acid or pyruvic acid contained therein. Rapid onset of the glycolysis-inhibiting action depending upon the pH change is believed to be due to rapid passive transport of the ions produced relative to the pH change so that pH in blood cells rapidly follows the change of pH in blood (outside blood cells).

According to the present invention, pH of blood which is normally 7.4 is adjusted to a level between 5.0 and 7.0 by the addition of an acid. The acid may be either inorganic or organic, but those organic acids are preferred which can be in powdered form and placed in a predetermined amount in sample-collection tubes for automatic mixing with blood when collected in the tube thereby easily producing an appropriate pH level.

Especially use of citric acid in an amount of 1.0-5.0 mg/ml (blood) is preferred, because it is excellent in buffer capacity, safe and easy to handle.

Moreover, combined use of addition of a fluoride compound, for example, NaF with the adjustment of pH by the use of an acid further improves the glycolysis-inhibiting action. Whereas amount of the NaF is 1.25 mg/ml in the prior-art methods, a very small amount as low as 0.1-0.5 mg/ml is sufficient in the method of the invention.

The present invention is carried out by placing in a collection tube in which, for example, 1.5-2.0 ml of blood is collected an aqueous solution principally consisting of citric acid and NaF in an amount sufficient to give the above-defined concentrations when mixed with the blood, evaporating the water from the solution and leaving the components in powdered form at the bottom of the tube. EDTA·2Na (disodium ethylenediaminetetraacetate) may be added to the solution as a filler or auxiliary for granulation. As EDTA·2Na has a blood-anticoagulant activity, it is useful also for such purpose. It is suitable to use EDTA·2Na in an amount between 1-5 mg/ml (blood) when used as the filler or auxiliary for granulation and in an amount between 1-2 mg/ml (blood) when used as the blood-anticoagulant. In a collection tube in which the abovementioned components are contained is collected 1.5-2.0 ml of blood, which is stored as it is for the determination of glucose, lactic acid or pyruvic acid contained therein.

The present invention will be described in more details by means of the following examples.

EXAMPLE 1

Citric acid and EDTA·2Na were added to and mixed in sample-collection tubes in such amounts that citric acid at 5 mg/ml (blood) and EDTA·2Na at 2 mg/ml (blood) were produced when blood was collected therein. pH of the blood which was originally 7.4 was changed to 5.8 after the addition.

The samples were incubated at 30° C. and measured for glucose at an interval of 3 hours. The glucose level (blood sugar) remained unchanged up to 12 hours. It was reduced by 5% after 24 hours and by 10% after 48 hours.

EXAMPLE 2

In the same way as in Example 1, 1N solution of acetic acid at 20 $\mu$l/ml and EDTA·2Na at 2 mg/ml (blood) were mixed with blood samples. pH of the blood which was originally 7.4 was changed to 5.8.

The samples were incubated at 30° C. and measured for glucose level (blood sugar level) at an interval of 3 hours. It was found that the blood sugar level remained unchanged up to 12 hours. 5% reduction was observed after 24 hours.

EXAMPLE 3

In the same way as in Example 1, citric acid at 2 mg/ml, NaF at 0.1 mg/ml and EDTA·2Na at 2 mg/ml (blood) were mixed with blood samples. pH of the blood which was originally 7.4 was changed to 6.8.

The samples were incubated at 30° C. and measured for glucose (blood sugar) at an interval of 3 hours. It was found that the blood sugar level remained unchanged up to 48 hours. 5% reduction of the blood sugar level was observed after additional incubation up to 72 hours.

EXAMPLE 4

In 5-ml blood-collection tubes was collected 2 ml of blood respectively in such a way that citric acid at 3.4 mg/ml, sodium citrate at 1.6 mg/ml, EDTA·2Na at 4.7 mg/ml and NaF at 0.3 mg/ml (blood) were contained therein. pH of the blood was changed from 7.4 to 5.2. Relationship between glucose concentration and storage time is shown in FIGS. 1 and 2 when the resulting blood samples were stored at 37° C. and room temperature, respectively. For comparison, results of the measurements using VENOJECT (FH) (tradename of a product manufactured by Terumo K.K.) in which NaF at 1.25 mg/ml, heparin Na at 12.5 U/ml and EDTA·2Na at 3.7 mg/ml (blood) were contained are shown in FIG. 1 or FIG. 2.

EXAMPLE 5

In 5-ml blood-collection tubes was collected 2 ml of blood in such a way that malonic acid at 5 mg/ml and EDTA·2Na at 2 mg/ml (blood) were contained therein. pH of the blood was changed from 7.4 to 5.2.

EXAMPLE 6

In 5-ml blood-collection tubes was collected 2 ml of blood in such a way that maleic acid at 5 mg/ml and EDTA·2Na at 2 mg/ml (blood) were contained therein. pH of the blood was changed from 7.4 to 5.3. Changes of glucose concentration (blood sugar level) in the blood samples in Examples 1-6 when stored at room temperature are shown in Table 1.

TABLE 1

| | Changes of blood sugar level | | | | | | | | | | |
|---|---|---|---|---|---|---|---|---|---|---|---|
| | Hours | | | | | | | | | | |
| | 0 | 3 | 6 | 9 | 12 | 15 | 18 | 21 | 24 | 48 | 72 |
| Example 1 | 103 | 103 | 103 | 102 | 103 | 103 | 102 | 100 | 98 | 93 | — |
| 2 | 105 | 105 | 105 | 105 | 105 | 105 | 104 | 102 | 100 | — | — |
| 3 | 110 | 110 | 110 | 109 | 110 | 109 | 110 | 110 | 110 | 110 | 105 |
| 4 | 101 | 101 | 101 | 101 | 101 | 101 | 100 | 101 | 101 | 101 | 100 |
| 5 | 105 | 105 | 104 | 105 | 104 | 105 | 102 | 100 | 99 | — | — |
| 6 | 100 | 100 | 100 | 101 | 100 | 99 | 100 | 98 | 96 | — | — |

As described in details above, the present invention is directed to a method of inhibiting glycolysis in blood samples for the determination of glucose, lactic acid or pyruvic acid contained therein simply by adding an acid, particularly citric acid to adjust pH of the blood to a level between 5.0 and 7.0, which provides correct values even when stored for dozens of hours after collection prior to the analytical operation. It is very effective in the determination of blood sugar level especially when a large number of samples are to be tested. The method is more effective due to duration of the glycolysis-inhibiting action by combined use of a fluoride compound added in a minimum amount.

What is claimed is:

1. A method of inhibiting glycolysis in blood samples which comprises adding an acid to the blood sample to adjust pH of the blood to a level between 5.0 and 7.0.

2. A method of inhibiting glycolysis according to claim 1 wherein the acid used is citric acid.

3. A method of inhibiting glycolysis according to claim 2 wherein citric acid is added to produce a concentration between 1.0 and 5.0 mg/mLbN (blood).

4. A method of inhibiting glycolysis according to any of claims 1–3 wherein a fluoride compound is added besides the acid.

5. A method of inhibiting glycolysis according to claim 4 wherein NaF is added to produce a concentration between 0.1–0.5 mg/ml (blood).

6. A method of inhibiting glycolysis according to claim 1 wherein the acid is added to the blood sample to adjust the pH of the blood to a level between 5.0 and 6.8.

* * * * *